United States Patent [19]

Sugimori

[11] Patent Number: 4,823,087
[45] Date of Patent: Apr. 18, 1989

[54] SALIMETER

[75] Inventor: Hideo Sugimori, 12-2, Koaza Shimokubota, Ohaza Hohsono, Seikacho, Sohraku-gun, Kyoto 619-02, Japan

[73] Assignees: Hideo Sugimori, Kyoto; Merbabu Corporation, Osaka, both of Japan

[21] Appl. No.: 5,490

[22] Filed: Jan. 16, 1987

[51] Int. Cl.[4] .................. G01N 27/22; G01N 27/42
[52] U.S. Cl. .................... 324/441; 324/439; 324/65 R; 324/62
[58] Field of Search .............. 340/347 NT; 324/62, 324/441, 439, 443, 444, 446, 65 R

[56] References Cited

U.S. PATENT DOCUMENTS

| 3,710,237 | 1/1973 | Watson | 324/446 |
| 3,774,104 | 11/1973 | Andersen | 324/441 |
| 3,836,847 | 9/1974 | Lucas | 324/62 |
| 4,303,887 | 12/1981 | Hill | 324/441 |
| 4,362,994 | 12/1982 | Goldsmith | 324/446 |
| 4,383,221 | 5/1983 | Morey | 324/441 |

Primary Examiner—Reinhard J. Eisenzopf
Assistant Examiner—Jose M. Solis
Attorney, Agent, or Firm—Koda and Androlia

[57] ABSTRACT

A salimeter based on the electric conductivity measurement of an objective liquid solution and devised so as to give the salinity of the solution instantly without any correction or adjustment with respect to a temperature of the solution. The apparatus is divided into a main electronic circuit portion and a measuring probe or probes to be detachably connected to the main circuit portion through a connecting cable. Each of the probes is provided with a pair of electrodes and a temperature sensor, both to be immersed directly in an objective solution, while the main circuit portion comprises a first means for measuring the conductivity between the electrodes, a second means for generating a temperature effect compensation signal according to an output from the temperature sensor and an arithmetic divider for outputting a ratio of the measured conductivity to the temperature effect compensation signal. The ratio, which gives the conductivity of the solution at a predetermined standard temperature, is converted to a corresponding value of salinity and then displayed on a display unit.

4 Claims, 4 Drawing Sheets

SALIMETER

BACKGROUND OF THE INVENTION

The present invention relates to a salimeter, and more particularly to a salimeter for determining the salinity of saline solution through the measurement of the electric conductivity of the solution.

Based on the fact that the salinity of a saline solution is inseparably related to the electric (ionic) conductivity of the solution, one well-known type of salimeter is by means of measuring the electric conductivity of an objective solution. Salimeters of this type fundamentally consist of an exciting AC voltage source and a pair of electrodes. The pair of electrodes is either constituted in the form of a probe capable of being immersed directly in an objective solution or provided in a measuring cell into which the objective solution is to be sampled. The exciting AC voltage source supplies an AC voltage between the electrodes with the probe immersed in an objective solution or with the solution sampled into the cell. The conductivity of the solution is obtained, in principle, from the data of the voltage and current between the electrodes and of the geometry of the pair of electrodes. In practice, the apparatus is devised so as to give a resultant value of the conductivity and/or salinity of the solution according to a probe or cell constant reflecting the geometry of the pair of electrodes. However, the exciting AC voltage, which should be kept constant in principle, must be corrected against possible small variations in the probe/cell constants of individual probes or cells in use.

Such an inconvenience is improved, for example, with the conductivity measuring apparatus disclosed in the Japanese Utility Model Application No. 56-65478. This apparatus is characterized by being provided with a reference resistor for use in calibrating the apparatus, in advance, against the errors resulting from the possible cell-constant variations with respect to the cells to be used. The reference resistor is incorporated so that it may be substituted for the cell through a switch operation. The incorporation of the reference resistor in the apparatus makes an easy and precise calibration possible. Furthermore, the circuit constitution of the apparatus provides another advantage that, once the calibration is made with respect to a specific cell, the conductivity measurements with the cell are secured from the possible voltage variations expected to the exciting AC voltage source, since the exciting voltage can easily be corrected.

However, there are left some problems in applying the above-mentioned improved conductivity measuring apparatus to a salimeter under consideration, though it is also based on the same principle of conductivity measurement, since the above apparatus has been improved only to make it easy to correct the excitation voltage against the variation in the cell constant. Because the conductivity of a solution depends on temperature, a solution with a constant salinity shows different values of conductivity according to the temperature of the solution. In order to obtain a proper salinity at a predetermined standard temperature (of 25° C.), therefore, it is necessary to provide a temperature sensor and an arithmetic means for correcting the measured conductivity in accordance with the temperature and conductivity temperature-coefficient of the solution. However, the addition of such correcting means to the above apparatus has effect also on the excitation voltage correction to be made by the adjustment of the reference resistor, causing the reference resistor to be useless at temperatures other than the standard temperature (25° C.). A further disadvantage is that the standard solution must always be reserved.

OBJECTS AND SUMMARY OF THE INVENTION

The present invention aims at eliminating the above mentioned disadvantages accompanying the conventional salimeters, and makes it an object to provide an improved salimeter capable of measuring a precise salinity of an objective solution without keeping the same at a standard temperature and, in addition, without necessitating a standard solution to be always reserved after the initial calibration procedures have been completed.

Another object of the present invention is to constitute such an improved salimeter with a main electronic circuit portion and a measuring probe portion detachably connected to the main portion through a prolonged connecting cable for the purpose of making a common salimeter applicable to widely diverging kinds of objective solutions, for which the use of a common probe is to be avoided. By providing a plurality of probes carrying their respective pairs of electrodes to be immersed in their respective specific kinds of solutions, a common salimeter can be used for various solutions ranging from a soup to be kept at a well sanitary condition to the liquid wastes from human or animal bodies.

A further object of the present invention is to assemble such an improved salimeter substantially in analog circuits to avoid the possible errors expected in digitalizing analog signals related to the conductivity and temperature data.

According to the present invention, a salimeter consists of a main electronic circuit portion and at least one detachable probe in which a pair of electrodes and a temperature sensor are provided to be immersed directly in an objective liquid solution. The main electronic circuit portion comprises an exciting AC voltage generator whose output is made adjustable, an amplifier for amplifying the output of the exciting AC voltage generator in proportion to the conductance (of the solution) between the electrodes provided in said probe, a rectifier for rectifying the output of the amplifier, a compensation signal generator for generating a temperature effect compensating signal in accordance with an output of said temperature sensor incorporated in the probe, an arithmetic divider for dividing the output of the rectifier by the output of the compensation signal generator, a display unit for displaying an output of the arithmetic divider, a reference resistor made capable of being substituted for the pair of electrodes, and a voltage source for providing a standard voltage capable of being inputted to the compensation signal generator substitutionally for the output from the temperature sensor.

BRIEF DESCRIPTION OF THE DRAWINGS

The details of the present invention are described in the following on reference to the accompanying drawings, in which.

DETAILED DESCRIPTION OF THE INVENTION

Figure 1:
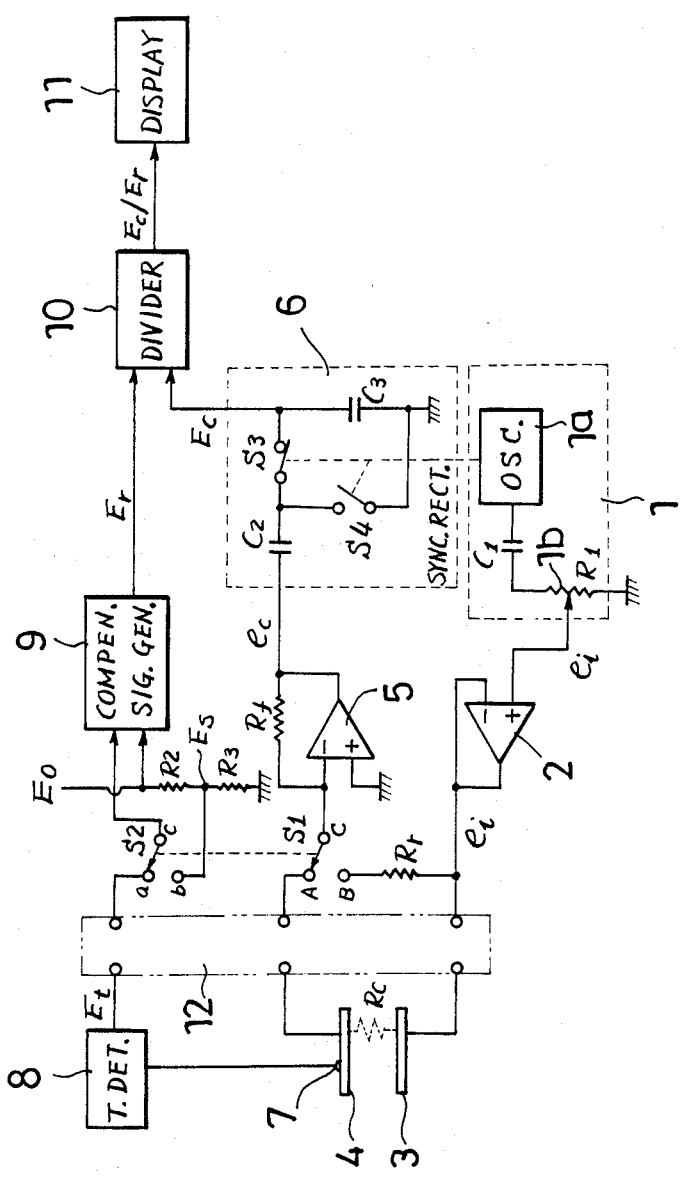
FIG. 1 shows a block-diagrammatic circuit constitution of an embodiment of the present invention.
Figure 4:
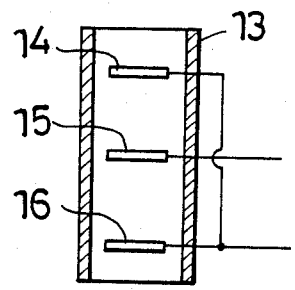
FIG. 4 shows the measuring probe used in the above embodiments shown in FIGS. 1, 2 and 3.
Figure 5:
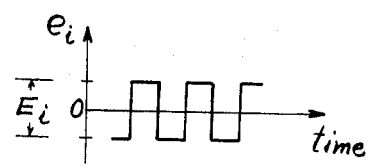
FIG. 5 shows the wave form of the output voltage from the exciting AC voltage source used in the above embodiments shown in FIGS. 1, 2 and 3.

Referring to FIG. 1, which shows the circuit constitution of an embodiment of the present invention, an exciting AC voltage source 1 consisting of an oscillator 1a and an output attenuator 1b supplies an exciting voltage $e_i$ to an electrode 3 through a buffer amplifier 2 with a gain of unity. The electrode 3, together with another electrode 4, constitutes a pair of electrodes to be immersed in an objective solution whose salinity is to be measured. A resistance $R_c$ shown between the electrodes 3 and 4 with a dotted line represents resistance expected to appear there when the pair of electrodes 3, 4 is immersed in a solution. The electrode 4 is connected to the inverting input terminal of an operational amplifier 5 through a switch S1. The operational amplifier 5 constitutes an inverting linear amplification circuit together with the resistance $R_c$ and a feed-back resistance $R_f$ connecting between the output and inverting input terminals of the operational amplifier 5. The output from the amplifier 5 is led to a synchronous rectifier circuit 6 consisting of two capacitors $C_2$, $C_3$ and two switching means S3 and S4. With the switching means S3 and S4 alternately operated in synchronous with the output frequency of the oscillator 1a, the rectifier circuit 6 rectifies an AC output voltage $e_c$ from the amplifier 5 and outputs a DC voltage $E_c$ equal to the peak-to-peak value of $e_c$. On the other hand the electrode 4 is provided with a temperature sensor 7 connected to a temperature detecting circuit 8, which outputs a temperature signal voltage $E_t$ proportional to the temperature t of the solution whose salinity is to be measured. The output $E_t$ of the temperature detecting circuit 8 is inputted through a switch S2 to a temperature effect compensation signal generating circuit 9, which outputs a compensation signal $E_r$ proportional to $1+\alpha(t-t_s)$, where $\alpha$ is a temperature coefficient of the conductance (and therefore, of the conductivity) of the saline solution and $t_s$ is a predetermined standard temperature value. Both the compensation signal $E_r$ and the output $E_c$ from the synchronous rectifier circuit 6 are inputted to an arithmetic divider circuit 10, which outputs a ratio $E_c/E_r$. The ratio $E_c/E_r$, which, as is described later, is proportional to the salinity of the objective solution, is displayed by a display unit 11. The salimeter according to the present invention further comprises a reference resistance $R_r$ and means for providing a standard voltage $E_s$ which corresponds to a predetermined standard temperature value. The means consists of a series connection of resistances $R_2$ and $R_3$, which divide a constant voltage $E_o$ to give the standard voltage $E_s$. This standard voltage $E_s$ is to be inputted, in substitution for the temperature signal $E_t$, to the temperature effect compensation signal generating circuit 9 through the switch S2, while the reference resistance $R_r$ is to be substituted for the pair of electrodes 3 and 4, namely, for the resistance $R_c$. In the above circuit constitution the exciting AC voltage source 1 outputs an AC voltage $e_i$ as shown in FIG. 5. Furthermore, the pair of electrodes 3 and 4 is constituted in the form of a probe 13 as shown in FIG. 4, in which equipotentially connected electrodes 14, 16 and single electrode 15 correspond to the electrodes 3 and 4 shown in FIG. 1. The probe is to be immersed in an objective solution.

Next, the use and function of the embodiment are described in the following.

Figure 6:
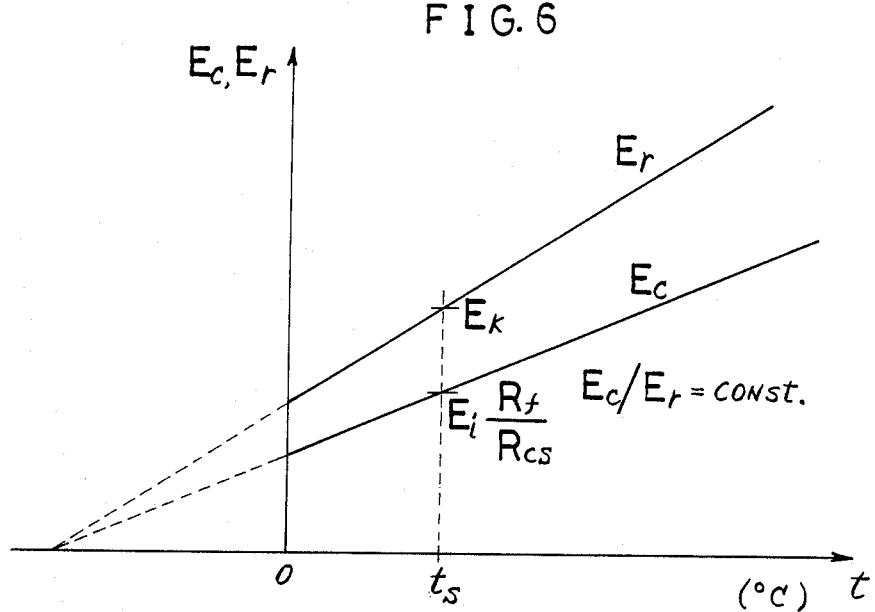
FIG. 6 is a graphic representation of temperature-dependent electric signals illustrating the function of the above embodiments shown in FIG. 1, 2 and 3.

In the first place the pair of electrodes 3 and 4 (formed into a single probe as shown in FIG. 4 as is mentioned above) is immersed in a standard solution with the switches S1 and S2 turned to contacts A and a, respectively. The standard solution is, for instance, a pure NaCl solution having a concentration of 5%. Thereupon the linear amplification circuit (consisting of the resistance $R_c$ of the standard solution, the feed-back resistance $R_f$ and the operational amplifier 5 outputs an AC voltage given by:

$$e_c = -e_i \frac{R_f}{R_{cs}} [1 + \alpha(t - t_s)], \qquad (1)$$

where $R_{cs}(=R_c)$ is the resistance of the standard solution at the predetermined standard temperature $t_s$, which is often chosen to be 25° C. Then, the synchronous rectifier circuit 6 rectifies the AC voltage given by Eq. (1) to output a DC voltage $E_c$ which is equal to the peak-to-peak value of $e_c$:

$$E_c = E_i \frac{R_f}{R_{cs}} [1 + \alpha(t - t_s)], \qquad (2)$$

where $E_i$ is the peak-to-peak value of $e_i$ (refer to FIG. 5), and $R_{cs}$ is the value of $R_c$ which the standard solution shows at the standard temperature. On the other hand the temperature detecting circuit 8 outputs a temperature signal voltage $E_t$ corresponding to the temperature t of the standard solution. The signal voltage $E_t$ is inputted to the temperature effect compensation signal generating circuit 9 to make it output a temperature effect compensation signal voltage $E_r$ given by the following Eq. (3) having the same temperature coefficient as that included in $E_c$ given by Eq. (2):

$$E_r = E_k[1 + \alpha(t - t_s)], \qquad (3)$$

where a proportionality factor $E_k$ is chosen to be equal to the value of $E_r$ at the standard temperature value. Eqs. (2) and (3) are graphically shown in FIG. 6. Their respective constant gradients give a constant ratio $E_c/E_r$ in the entire range of temperature.

The above two voltages $E_c$ and $E_r$ are inputted to the arithmetic divider circuit 10, which performs an arithmetic operation of dividing $E_c$ by $E_r$ giving a ratio:

$$E_c/E_r = \frac{E_i R_f}{E_k} \cdot \frac{1}{R_{cs}}. \qquad (4)$$

As is shown by Eq. (4), the ratio $E_c/E_r$ does not contain a temperature term and is proportional to the peak-to-peak value $E_i$ of the exciting voltage $e_i$ and the conductance $1/R_{cs}$ of the standard solution at the predetermined standard temperature. The ratio $E_c/E_r$ is to be inputted to the display unit 11 to display the salinity. In this case the ratio $E_c/E_r$ is made equal to the salinity value itself (5% in the present case) of the standard solution by adjusting $E_i$ through the operation of the attenuator 1b provided in the exciting AC voltage source 1. Once $E_i$ is adjusted so as to make the display unit 11 display the salinity value of the standard solution, the salimeter is calibrated so as to show the value of salinity also with respect to any other objective solution. Incidentally, an A-D converter can be used as the above arithmetic divider 10 by inputting $E_c$ thereto as a signal to be converted with $E_r$ used as a reference signal.

Further, the present invention is devised so that, even if the $E_i$-adjustment is put out of order for some reason or other, the calibration may easily be recovered without using the standard solution again. Just after the $E_i$ adjustment is made for calibration, turn the switches S1 and S2 respectively to contacts B and b, and then read and take notes of the reading on the display unit 11. This ratio $E_c/E_r$ displayed at this time is the value obtained with $E_s$ and $R_r$ substituted respectively for $E_k$ and $R_{cs}$ in Eq. (4), resulting in:

$$E_c/E_r = \frac{E_i R_f}{E_s} \cdot \frac{1}{R_r} . \quad (5)$$

Because $R_f$, $E_s$ and $R_r$ are constant, the ratio is determined only by a set value of the excitation voltage $E_i$, giving a value proportional to a probe constant with the variation corrected. In case a plurality of probes are provided for various kinds of objective solutions, the above procedure of calibration should be taken in advance with respect to each of the probes.

Figure 2:
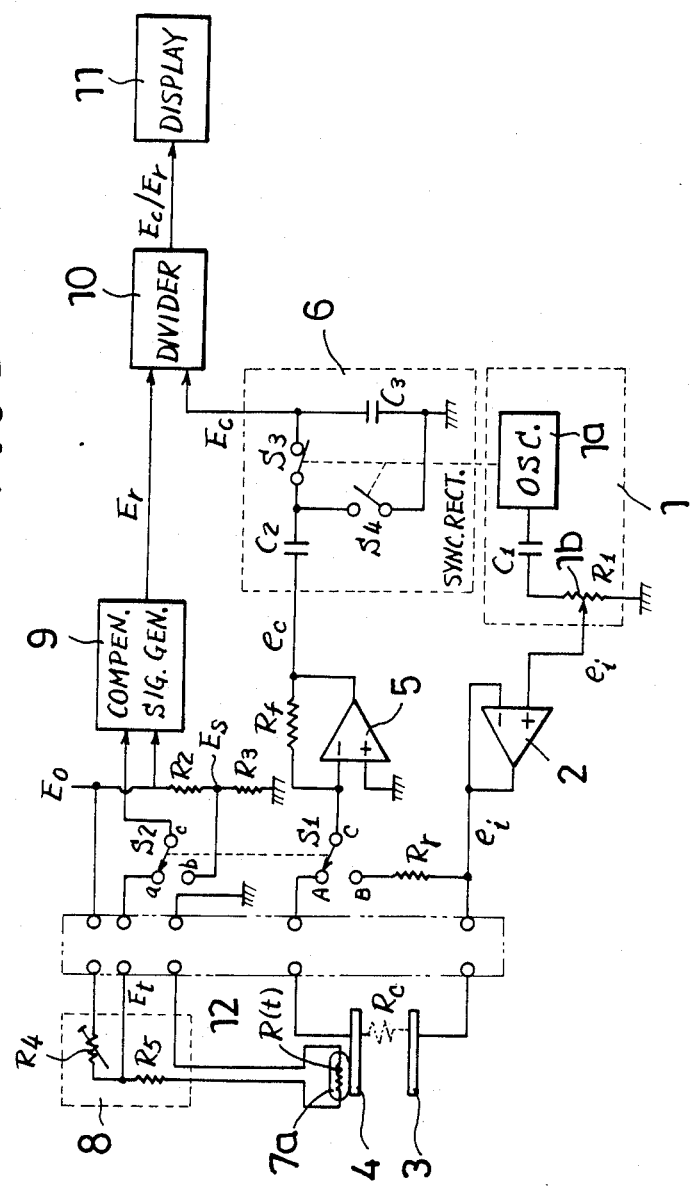
FIG. 2 shows a block-diagrammatic circuit constitution of another embodiment of the present invention.

Further, in case the temperature sensor is a resistance thermometer, the present invention can be modified as shown in FIG. 2. According to this embodiment the resistance thermometer 7a is supplied with an exciting current from the constant voltage $E_o$ (which is also the voltage source of $E_s$) through a variable resistance $R_4$ and a constant resistance $R_5$, outputting a voltage given by $E_o R(t)/(R_4+R_5 R(t))$ as the temperature signal voltage $E_t$, where $R(t)$ is the temperature-dependent resistance of the resistance thermometer 7a at a temperature t. According to such a circuit constitution of the thermometer exciting current supply system, possible $E_t$-variations due to characteristic variations of the individual resistance thermometers belonging the different probes (provided for various kinds of objective solutions) can be eliminated by correcting the thermometer characteristics through the adjustment of the variable resistance $R_4$.

Figure 3:
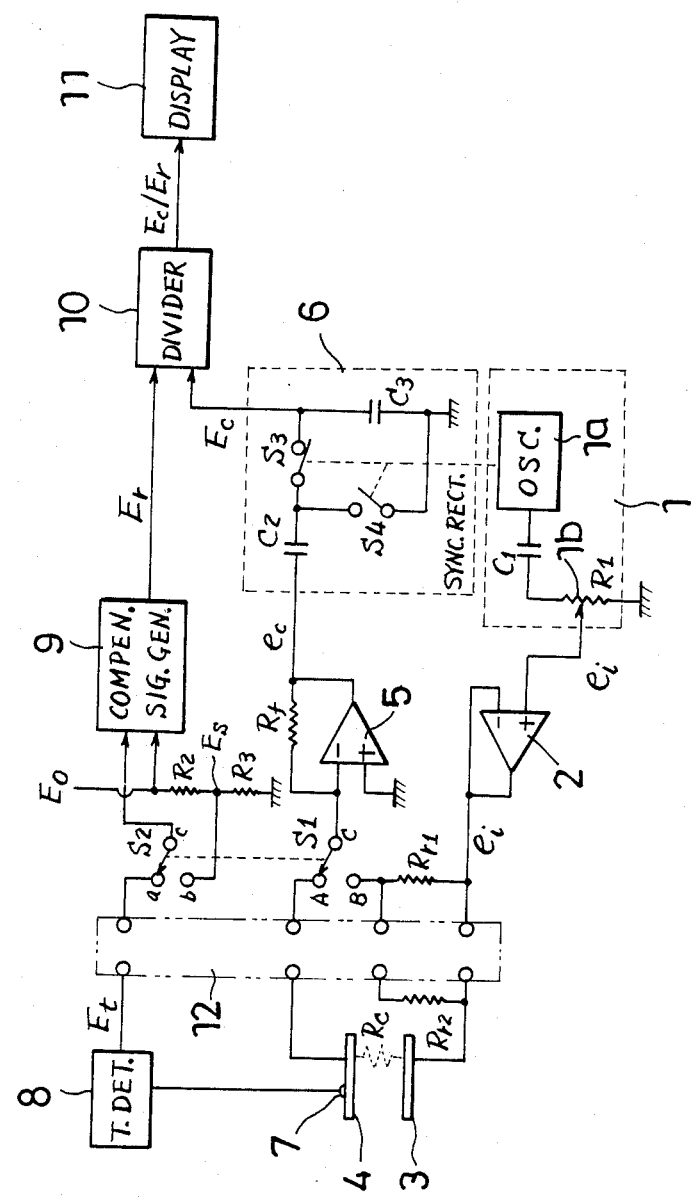
FIG. 3 shows a block-diagrammatic circuit constitution of a further embodiment of the present invention.

The present invention can be further embodied as shown in FIG. 3. In this embodiment the reference resistance $R_r$ is made up of a parallel connection of two resistances, namely, a constant resistance $R_{r1}$ and a semi-variable one $R_{r2}$: $R_{r1}$ is provided in the main circuit portion of the apparatus and $R_{r2}$ is placed in each of the probes. Thus, the reference resistance corresponding to $R_r$ in the embodiments shown in FIGS. 1 and 2 is given by $R_{r1} R_{r2}/(R_{r1}+R_{r2})$. Therefore, the calibration values displayed on the display unit 11 with the switches S1 and S2 turned respectively to the contacts B and b can be made equal irrespective of the variation in the probe constant of the individual probes by adjusting the variable resistance $R_{r2}$ in the calibration process with respect to each of the probes.

Further, the embodiments shown in FIGS. 1 and 2 can be modified by moving the reference resistance $R_r$ to each of the probes. In this case the moved resistance $R_r$ is made variable to be adjusted in advance in accordance with the probe constant of each probe.

I claim:

1. A salimeter for detecting the salinity of a liquid solution through measuring the electric conductivity of said liquid solution and normalizing the same to the value expected at a predetermined standard temperature by the use of a means for compensating the effect of temperature on the electric conductivity, said means being included in said salimeter, said salimeter comprising:

an AC voltage source for supplying an exciting AC power necessary to measure the conductivity of an objective liquid solution whose salinity is to be detected, said AC voltage source being provided with an output voltage adjusting means;

a pair of electrodes to be immersed in said objective liquid solution;

an amplifying means for outputting a voltage proportional to the electric conductance developed in said pair of electrodes when the same is immersed in a liquid solution;

a reference resistor capable of being electrically substituted for said pair of electrodes;

a temperature detecting means for detecting the temperature of the liquid solution in which said pair of electrodes is immersed;

a temperature effect compensation voltage generating circuit devised so as to output, in accordance with the output voltage from said temperature detecting means, a voltage proportional to $1+\alpha(t-t_s)$, where $\alpha$, t and $t_s$ are respectively the temperature coefficient of electric conductivity of saline solution, the temperature detected by said temperature detecting means and a predetermined standard temperature;

a reference voltage generating means whose output is made capable of being substituted for the output from said temperature effect compensation voltage generating means;

a first switching means capable of making said reference resistor electrically substituted for said pair of electrodes;

a second switching means for selectively inputting either of the output from said temperature detecting means or the output from said reference voltage generating means to said temperature effect compensating voltage generating circuit;

an arithmetic divider for dividing the output from said amplifying means by the output from said temperature effect compensation voltage generating circuit; and a display unit for displaying the value proportional to the output from said arithmetic divider.

2. A salimeter defined in claim 1, wherein said amplifying means consists of an AC amplifier and a rectifier for rectifying the output from said AC amplifier, while said AC amplifier is an inverting type linear amplifier using an IC operational amplifier with its input resistor normally replaced by said pair of electrodes, through which an AC voltage is supplied from said AC voltage source, and wherein said reference resistor has a resistance equal to the resistance developed in said pair of electrodes when the same is immersed in a standard liquid solution having a predetermined standard salinity; and said reference voltage generating means outputs a voltage equal to the value outputted from said temperature detecting means when the same detects a predetermined standard temperature.

3. A salimeter defined in claim 1 or 2 wherein said salimeter is constituted in two separate portions: one is a main portion from which only said pair of electrodes and said temperature detecting means are excluded, and the other is a detachable portion consisting of said pair of electrodes and said temperature detecting means and wherein said pair of electrodes is constituted in the form of a probe to be immersed in an objective liquid solution, said probe, together with said temperature detecting means being made detachably connectable to said main portion through a cable.

4. A salimeter defined in claim 3, wherein said reference resistor is divided into two parallel resistors: one is a semi-variable subsidiary resistor located in said detachable portion and the other is a fixed main resistor located in said main portion.

* * * * *